United States Patent
Embrey et al.

(10) Patent No.: US 8,673,583 B2
(45) Date of Patent: Mar. 18, 2014

(54) MONOCLONAL ANTIBODIES AND DETECTION METHODS FOR ENZYMES THAT CONFER RESISTANCE TO 2,4-DICHLOROPHENOXYACETIC ACID

(75) Inventors: Shawna K. Embrey, Indianapolis, IN (US); Gaofeng Lin, Zionsville, IN (US); Guomin Shan, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 185 days.

(21) Appl. No.: 13/218,498

(22) Filed: Aug. 26, 2011

(65) Prior Publication Data

US 2012/0064542 A1 Mar. 15, 2012

Related U.S. Application Data

(60) Provisional application No. 61/383,015, filed on Sep. 15, 2010.

(51) Int. Cl.
| | |
|---|---|
| *G01N 33/573* | (2006.01) |
| *G01N 33/543* | (2006.01) |
| *C12Q 1/26* | (2006.01) |
| *C07K 16/40* | (2006.01) |
| *C07K 16/12* | (2006.01) |

(52) U.S. Cl.
CPC ............ *C07K 16/1203* (2013.01); *C07K 16/40* (2013.01); *G01N 33/573* (2013.01); *G01N 33/543* (2013.01); *G01N 2333/195* (2013.01); *G01N 2333/90* (2013.01); *G01N 2333/90241* (2013.01); *C12Q 1/26* (2013.01)
USPC ............ 435/7.4; 435/7.1; 435/7.94; 435/338; 530/388.1

(58) Field of Classification Search
None
See application file for complete search history.

(56) References Cited

U.S. PATENT DOCUMENTS

| | | | |
|---|---|---|---|
| 4,363,799 A | 12/1982 | Kung et al. | |
| 6,153,401 A | 11/2000 | Streber et al. | |
| 2009/0093366 A1 | 4/2009 | Wright et al. | |
| 2011/0191899 A1* | 8/2011 | Ainley et al. | ............. 800/278 |
| 2011/0289620 A1* | 11/2011 | Cui et al. | ............. 504/142 |
| 2012/0222153 A1* | 8/2012 | Cui et al. | ............. 800/275 |

FOREIGN PATENT DOCUMENTS

| | | |
|---|---|---|
| WO | WO 2005/107437 | 11/2005 |
| WO | WO 2011/153300 | 12/2011 |

OTHER PUBLICATIONS

Wright et al. "Robust crop resistance to broadleaf and grass herbicides provided by aryloxyalkanoate dioxygenase transgenes", Proceedings of the National Academy of Sciences, vol. 107 No. 47 (Published online before print Nov. 23, 2010), pp. 20240-20245, and additional three (3) pages of accompanying online Supporting Information.*

Database Genbank, Accession No. M16730, Streber, W.R. et al, "Analysis, cloning, and high-level expression of 2,4-dichlorophenoxyacetate monooxygenase gene tfdA of *Alcaligenes eutrophus* JMP134" Apr. 26, 1993, pp. 1-2.

Written Opinion in International Application No. PCT/US2011/49263, Mar. 16, 2012, pp. 1-3.

* cited by examiner

*Primary Examiner* — Christine Foster
(74) *Attorney, Agent, or Firm* — Ronal S. Maciak; Saliwanchik, Lloyd & Eisenschenk (57) ABSTRACT

Described herein are monoclonal antibodies and methods useful for determining and quantitating the presence of AAD-1 (aryloxyalkanoate dioxygenase) enzyme. These monoclonal antibodies are surprisingly well suited for detecting AAD-1 transgenic event gene products in a variety of plants and plant tissues. The invention further provides quantitative and qualitative immunoassays using the immunoglobulins of the invention.

19 Claims, 1 Drawing Sheet

MONOCLONAL ANTIBODIES AND DETECTION METHODS FOR ENZYMES THAT CONFER RESISTANCE TO 2,4-DICHLOROPHENOXYACETIC ACID

CROSS-REFERENCE TO RELATED APPLICATION

This application claims the benefit of U.S. Provisional Application Ser. No. 61/383,015, filed Sep. 15, 2010, the disclosure of which is hereby incorporated by reference in its entirety, including all figures, tables and amino acid or nucleic acid sequences.

BACKGROUND OF THE INVENTION 2,4-dichiorophenoxyacetic acid (2,4-D) is in the phenoxy acid class of herbicides and has been used in many monocot crops such as corn, wheat, and rice for the selective control of broadleaf weeds without severely damaging the desired crop plants. 2,4-D is a synthetic auxin derivative that acts to deregulate normal cell-hormone homeostasis and impede balanced, controlled growth; however, the exact mode of action of this class of herbicides is still not fully understood, despite more than 60 years of field application. Triclopyr and fluroxypyr are pyridyloxyacetic acid herbicides that also act as a synthetic auxin.

These herbicides have different levels of selectivity on certain plants (e.g., dicots are more sensitive than monocots). Differential metabolism by different plants is one explanation for varying levels of selectivity. In general, plants metabolize 2,4-D slowly, so varying plant response to 2,4-D may be more likely explained by different activity at the target sites (WSSA, 2002; Herbicide Handbook 8$^{th}$ edition; Weed Science Society of America; Lawrence, Kans. pp. 492.) Plant metabolism of 2,4-D typically occurs via a two-phase mechanism, typically hydroxylation followed by conjugation with amino acids or glucose (WSSA, 2002).

Over time, certain microbial populations challenged with 2,4-D have developed an alternate pathway for degrading this xenobiotic that results in the complete mineralization of 2,4-D. Successive applications of the herbicide select for microbes that can utilize the herbicide as a carbon and energy source for growth, giving them a competitive advantage in the soil. For this reason, currently formulated 2,4-D has a relatively short soil half-life and no significant carryover effects on subsequent crops.

One organism that has been extensively studied for its ability to degrade 2,4-D is *Ralstonia eutropha* (Streber, et al; 1987; Analysis, cloning, and high-level expression of 2,4-dichlorophenixyacetic monooxygenase gene tfdA of *Alcaligenes eutrophus* JMP134. J. Bacteriol. 169:2950-2955). The gene encoding the enzyme in the initial step of the mineralization pathway is tfdA. See U.S. Pat. No. 6,153,401 and GENBANK Acc. No. M16730. The TfdA gene product catalyzes the conversion of 2,4-D to dichlorophenol (DCP) via an α-ketoglutarate-dependent dioxygenase reaction (Smejkal; et al.; 2001. Substrate specificity of chlorophenoxyalkanoic acid-degrading bacteria is not dependent upon phylogenetically related tfdA gene types. Biol. Fertil. Sols 33:507-513). DCP has little herbicidal activity compared to 2,4-D. TfdA has been used in transgenic plants to impart 2,4-D resistance in dicot plants such as cotton and tobacco which naturally sensitive to 2,4-D (Streber; et al.; 1989. Transgenic tobacco plants expressing a bacterial detoxifying enzyme are resistant to 2,4-D. Bio/Technology 7:811-816), and U.S. Pat. No. 5,608,147).

A large number of tfdA-type genes that encode enzymes capable of degrading 2,4-D have been isolated from soil bacterial and their sequences deposited into the Genbank database. Many homologues of tfdA (>85% amino acid identity) have similar enzymatic properties to tfdA. However, there are a number of homologues that have a significantly lower identity to tfdA (25-50%), yet have the characteristic residues associated with α-ketoglutarate dioxygenase Fe$^{+2}$ dioxygenases. Thus it is not obvious what the substrate specificities of these divergent dioxygenases are, among other biochemical properties.

One unique example with low homology to tfdA (28% amino acid identity) is rdpA from *Sphingobium herbicidovorans* (Kohler, H. P. E. 1999. *Sphingobium herbicidovorans* MH: a versatile phenoxyalkanoic acid herbicide degrader. J. Ind Microbiol and Biotech. 23:336-340, Westendorf A., D. Benndorf, R. Muller, W. Babel. 2002. The two enantiospecific dichlorprop/α-ketoglutarate-dioxygenases from *Delftia acidovorans* MC1-protein and sequence data of RdpA and SdpA., Microbiol. Res. 157:317-22). This enzyme has been shown to catalyze the first step in (R)-dichlorprop (and other (R)-phenoxypropionic acids) as well as 2,4-D (a phenoxyacetic acid) mineralization (Westendorf, A., R. H. Muller, and W. Babel. 2003. Purification and characterization of the enantiospecific dioxygenases from *Delftia acidovorans* MC1 initiating the degradation of phenoxypropionates and phenoxyacetate herbicides. Acta Biotechnol. 23: 3-17). Although the organisms that degrade phenoxypropionic acid were described some time ago, little progress had been made in characterizing this pathway (Horvath, M., G. Ditzelmuller, M. Lodl, and F. Streichsbier 1990). Isolation and characterization of a 2-(2,4-dichlorophenoxy) propionic acid-degrading soil bacterium. Appl. Microbiol. Biotechnol. 33:213-216). An additional complication to dichlorprop degradation is the stereospecificity (R vs. S) involved in both the uptake (Kohler, 1999) and initial oxidation of dichlorprop (Westendorf et al., 2003). Heterologous expression of rdpA in other microbes, or transformation of this gene into plants, has not heretofore been reported. Literature has focused mainly on close homologues of tfdA that primarily degrade achiral phenoxyacetic acids (e.g., 2,4-D).

A plant codon-optimized aryloxyalkanoate dioxygenase gene, AAD-1, that encodes the enzyme originally isolated from *Delftia acidovorans* was first describe for use as a herbicide resistance trait in WO 2005/107437, herein incorporated by reference. The trait confers tolerance to 2,4-D and to pyridyloxyacetate herbicides. The first report of transformed maize hearing the AAD-1 gene was in U.S. Provisional Patent Application No. 61/235,248, herein incorporated by reference.

Companies which develop and market recombinant DNA traits for planting seed products formulate, implement and adhere to strict product stewardship plans. These stewardship plans require the use of validated quantitative and qualitative protein detection methods for the recombinant trait to track trait introgression and seed production activities, as well as monitoring grain harvest for the trait. These detection methods must be facile and robust enough to use under GLP and non-GLP conditions. Moreover the methods must be user friendly and trouble-free enough to be easily employed by farmers in the field, grain dealers at the silo, and customs officials at the borders. Therefore, robust, high quality, user friendly protein detection methods and commercial kits are critical and essential to launching a recombinant plant trait product.

While immunoassays are well-known in the art, developing robust and validated ELISA (enzyme-linked immunosorbent assay) methods that are reproducible and sensitive enough to detect a particular transgenic product in an array of plant tissues in both lab and field settings is neither trivial nor routine. Still more challenging is to find complementary antibody pairs that are suited to the development of lateral flow strip ELISA methods for detecting the product of an AAD-1 transgenic event.

SUMMARY OF THE INVENTION

The present invention provides a panel of monoclonal antibodies (mAbs) and the hybridoma cell lines that produce the claimed antibodies. The hybridomas were deposited in the American Type Culture Collection (10801 University Boulevard Manassas, Va.) on Aug. 10, 2010 in accordance with the terms of the Budapest Treaty. The claimed mAbs are surprisingly well suited for detecting a specific AAD-1 transgenic event gene product in a variety of plants and plant tissues. The invention further provides quantitative and qualitative immunoassays using the claimed immunoglobulins of the invention.

DETAILED DESCRIPTION

The present invention encompasses antibodies reactive with AAD-1 and the hybridomas that produce the claimed mAbs. The table below lists the hybridoma line designations and their corresponding ATCC deposit designations.

| Hybridoma/mAb Designation | ATCC Deposit Designation | ATCC Deposit Date |
|---|---|---|
| 473F185.2#18 | PTA-11251 | 10 Aug. 2010 |
| 473F225.2#7 | PTA-11252 | 10 Aug. 2010 |
| 473F274.2#36 | PTA-11253 | 10 Aug. 2010 |
| 473H46.2 | PTA-11254 | 10 Aug. 2010 |
| 473H172.3 | PTA-11255 | 10 Aug. 2010 |

The invention also include methods of using the mAbs for isolating or detecting AAD-1 comprising: a) immobilizing said antibody onto a surface; b) contacting said immobilized antibody with a mixture containing AAD-1; c) separating said immobilized antibody bound to AAD-1 from said mixture; and d) recovering AAD-1 by removing the antibody-bound AAD-1 from said immobilized antibody.

The invention also includes a method of using the claimed antibodies for identifying the presence of AAD-1 in a biological sample comprising: a) immobilizing said antibody onto an assay surface; b) contacting said assay surface with a liquid suspected of containing AAD-1 and washing said assay surface with a suitable solution; c) contacting said assay surface with an anti-AAD-1 antibody labeled with a reporting group and washing said assay surface with a suitable solution; d) detecting the presence of said reporting group.

The invention further includes an analytical method for the quantitative determination of AAD-1 enzyme expressed in transgenic plants, especially maize and cotton plants. The AAD-1 protein is extracted from maize samples with a PBST (phosphate buffered saline with 0.05% TWEEN®-20) solution. The extract is centrifuged and the aqueous supernatant is collected and diluted. An aliquot of the diluted sample is incubated with enzyme-conjugated anti-AAD-1 monoclonal antibody in the wells of an anti-AAD-1 polyclonal or monoclonal antibody-coated plate in a sandwich ELISA format. Both antibodies in the sandwich pair capture the AAD-1 protein in the sample. At the end of the incubation period, the unbound reagents are removed from the plate by washing with PBST. The presence of AAD-1 is detected by incubating the enzyme conjugate with an enzyme substrate, generating a colored product. Since the AAD-1 is bound in the antibody sandwich, the level of color development is proportional to the concentration of AAD-1 in the sample (i.e., lower protein concentrations result in lower color development). The absorbance at 450 nm (or 405 nm depending on the label) minus absorbance at a reference wavelength (such as 650 nm) is measured using a plate reader. A calibration curve is estimated from seven standard concentrations using a quadratic regression equation. This AAD-1 ELISA is specific and sufficiently sensitive to quantitate AAD-1 in plant tissue sample extracts. In addition the antibodies of the invention may be used to confirm the presence of AAD-1 using known Western blotting techniques.

The preparation of monoclonal antibodies against proteins of interest is well known in the art. See Galfre and Milstein, Methods in Enzymology, Vol. 73, Academic Press, New York (1981); James W. Goding, Monoclonal Antibodies: Principles and Practice, Academic Press, Orlando, Fla. (1986); Current Protocols in Molecular Biolopy, F. M. Ausubel, et al. ed., Wiley Interscience, New York, (1987). While it may be routine to generate scores of mAbs reactive with a given immunogen, it is challenging to sort through them to find the very few mAbs that are suitable for a particular application and to ensure the hybridomas secreting them are stable and amenable to continuous culturing.

To prepare antibodies reactive with a protein of interest, the protein must be first enriched or purified. Relatively crude antigenic preparations of the protein may be used for immunization purposes. However, highly purified protein is required to determine accurately if hybridomas are producing the sought after monoclonal antibodies or to assay the antibody titers of specific sera.

Once the AAD-1 has been isolated, antibodies specific for AAD-1 may be raised by conventional methods that are well known in the art. Repeated injections into a host of choice over a period of weeks or months will elicit an immune response and result in significant anti-AAD-1 serum titers. Preferred hosts are mammalian species and more highly preferred species are rabbits, goats, sheep and mice. Blood drawn from such immunized animals may be processed by established methods to obtain antiserum (polyclonal antibodies) reactive with AAD-1. The antiserum may then be affinity purified by adsorption to AAD-1 according to techniques known in the art. Affinity purified antiserum may be further purified by isolating the immunoglobulin fraction within the antiserum using procedures known in the art. The resulting material will be a heterogeneous population of immunoglobulins reactive with AAD-1.

Anti-AAD-1 mAbs are readily prepared using purified AAD-1. Methods for producing mAbs have been practiced for several decades and are well known to those of ordinary skill in the art. Repeated intraperitoneal or subcutaneous injections of AAD-1 in adjuvant will elicit an immune response in most animals, especially mice. Hyperimmunized B-lymphocytes are removed from the animal and fused with a suitable fusion partner cell line capable of being cultured indefinitely. Numerous mammalian cell lines are suitable fusion partners for the production of hybridomas. Many such lines are commercially available from the ATCC and commercial suppliers.

Once fused, the resulting hybridomas are cultured in a selective growth medium for one to two weeks. Two well known selection systems are available for eliminating non-fused myeloma cells or fusions between myeloma cells from the mixed hybridoma culture. The choice of selection system depends on the strain of mouse immunized and myeloma fusion partner used. The AAT selection system, described by Taggart and Samloff, Science 219, 1228 (1982), may be used; however, the HAT (hypoxanthine, aminopterin, thymidine) selection system, described by Littlefield, Science 145, 709 (1964), is preferred because of its compatibility with mouse cells and fusion partners mentioned above.

Spent growth medium is then screened for immunospecific mAb secretion. Enzyme linked immunosorbant assay procedures are best suited for this purpose; though, radioimmune assays adapted for large volume screening are also acceptable. Multiple screens designed to consecutively pare down the considerable number of irrelevant or less desired cultures must be performed to isolate the small percentage of mAbs of the instant invention. Cultures that secrete mAbs reactive with AAD-1 were isotyped using commercially available kits.

Hybridoma cultures which secrete the sought-after anti AAD-1 mAbs should be subcloned several times to establish monoclonality and stability. Well known methods for sub-cloning eukaryotic, non-adherent cell cultures include limiting dilution, soft agarose and fluorescence activated cell sorting techniques. After each subcloning, the resultant cultures must be re-assayed for antibody secretion and isotyped again to ensure a stable antibody-secreting culture has been established.

The claimed anti-AAD-1 antibodies can be immobilized to a surface so that some of the antibody binding site remains exposed and capable of binding AAD-1. A wide assortment of schemes for immobilizing antibodies has developed over the past few decades. Immobilization can be accomplished by covalently coupling the antibody directly to the desired surface or by bridging the antibody to the surface.

CNBr and carbodiimide coupling of antibodies to polysaccharide based heads such as Sepharose® (GE Healthcare Bio-Sciences Corp.; Pisteataway, N.J.) are illustrative of direct coupling schemes that are consistent with the invention. Direct couplings generally do not orient the antibodies in any particular fashion; however, some types of direct couplings are able to reproducibly orient the antibody on the immobilizing substance.

Preferred coupling schemes orient the antibody such that its antigen binding regions remain exposed. One such scheme utilizes the natural carbohydrate found on the heavy chains of the antibody. By first oxidizing the carbohydrate moieties to the corresponding aldehydes, the reacting aldehydes further interact with a primary amino group on the matrix surface, it is possible to link the antibody in an advantageous orientation.

Many types of bridges are possible and include small organic linkers which covalently bind the antibody to the immobilizing substance. Such spacer arms are acceptable and preferably should not interact with proteins once the bridge has been formed.

The above discussion is in no way meant to limit the scope of the invention. Numerous other well known schemes for linking antibodies to immobilizing substances are consistent with the invention.

It is well known that antibodies labeled with a reporting group can be used to identify the presence of antigens in a variety of milieus. Antibodies labeled with radioisotopes have been used for decades in radioimmune assays to identify, with great precision and sensitivity, the presence of antigens in a variety of biological fluids. More recently, enzyme labeled antibodies have been used as a substitute for radiolabeled antibodies in the popular ELISA.

Antibodies of the present invention can be bound to an immobilizing substance such as a polystyrene well or particle and used in immunoassays to determine whether AAD-1 is present in a test sample. In this embodiment of the invention, a sample is contacted with the immunoaffinity surface and allowed to incubate. After a washing step, any AAD-1 that has bound to the immunoaffinity surface is detected by contacting the surface with another antibody of the invention labeled with a reporting group.

The use of lateral flow strips or immunochromatographic strips with the claimed antibodies and assay methods is consistent with the invention. Lateral flow assays are well known in the art. See for example U.S. Pat. No. 6,485,982. In this mode lateral flow tests can be used for qualitative or semi-quantitative detection of AAD-1 alone or simultaneously with other analytes. Lateral flow tests are the simplest to use of all the test formats described herein and are particularly useful in field settings where plant material is quickly extracted into a solution and tested on a lateral flow strip. In this mode it is only necessary to place the lateral flow strip into a liquid sample or to apply the liquid sample to the lateral flow strip and read the results after a predetermined time. All lateral flow tests should incorporate either a procedural control line or a sample control line that is used to validate the test result. Appearance of two lines, therefore, indicates a positive result, while a valid negative test produces only the control line. If only the test line appears, or if no lines appear, it is invalid.

A typical lateral flow test strip consists of four main components: a sample pad upon which the test sample is applied; a conjugate pad that contains antibodies of the present invention conjugated to colored particles (typically colloidal gold particles, or latex microspheres); a reaction membrane such as a hydrophobic nitrocellulose or cellulose acetate membrane onto which a different antibody of the invention is immobilized in a line across the membrane as a capture zone or test line; and lastly, a waste reservoir designed to draw the sample across the reaction membrane by capillary action.

The components of the lateral flow strip are normally fixed to an inert backing material and may be presented in a simple dipstick format or within a plastic casing with a sample port and reaction window showing the capture and control zones. In another mode of the assay embodiment, a test sample suspected of containing AAD-1 is dried onto a surface, forming an immobilized test sample. A labeled antibody of the invention is then contacted with the immobilized test sample and allowed to incubate, If the sample contains AAD-1, the labeled antibody will bind to the immobilized AAD-1. This method can also be done using an unlabeled antibody of the invention followed by a labeled secondary antibody that binds to an antibody of the invention which has already bound to AAD-1. After washing, the immobilized test sample is measured to detect the presence of any reporting groups.

Reporting groups are typically enzymes such as alkaline phosphatase, horseradish peroxidase or beta-D-galactosidase. Suitable substrates produce a color change when reacted with the enzyme. In so doing, measurements of the color intensity can be quantitated using a spectrophotometer. If the reporting group is a radioisotope, an appropriate gamma or beta ray detecting instrument can be used to quantify the reporting group. The intensity of the reporting group directly correlates, with the amount of AAD-1 in the test sample.

The following examples will help describe how the invention is practiced and will illustrate the characteristics of the claimed anti-AAD-1 antibodies and assays.

EXAMPLE 1

Immunogen Preparation

AAD-1 protein was extracted from lyophilized leaf tissue collected from transgenic maize in a PBST (Phosphate Buffered Saline with 0.05% TWEEN®-20, pH 7.4) based buffer with added stabilizers, and the soluble proteins were collected in the supernatant after centrifugation. The supernatant was filtered, adjusted to 1M AmSO$_4$ and the soluble proteins were allowed to bind to Phenyl Sepharose™ HIC (hydrophobic interaction beads) (GE Healthcare). After an hour of incubation, the HIC beads were washed with PBST and the bound proteins were eluted with Milli-Q™ water. Sodium chloride was added to increase the conductivity and the HIC purified proteins were loaded onto an anti-AAD-1 immunoaffinity column which had been conjugated with an AAD-1 specific polyclonal antibody. The polyclonal antibody was raised against recombinant AAD-1 produced in *Pseudomonas fluorescens* as described in WO2005/107437. The non-bound proteins were collected from the column and the column was washed extensively with pre-chilled PBS (phosphate buffered saline, pH 7.4). The bound proteins were eluted from the column with a 3.5 M NaSCN, 50 mM Tris™, pH 8.0 buffer. Microbial-derived AAD-1 and maize-derived AAD-1 were examined by SDS-PAGE and western blotting.

In the microbe-derived AAD-1, the major protein band, as visualized on the Coomassie stained SDS-PAGE gel, was approximately 32 kDa. The corresponding plant-derived AAD-1 protein was identical in size to the microbe-derived protein. In addition, the plant-derived AAD-1 sample contained a minor amount of impurity, which was non-immunoreactive to the AAD-1 antiserum. The co-purified proteins were likely retained on the column by the weak interactions with the column matrix.

The microbe-derived AAD-1 and plant-derived sample showed a positive signal of the expected size on the Western blot using anti-AAD-1 antiserum. In the AAD-1 western blot analysis, no immunoreactive proteins were observed in negative control (native maize) extract, nor alternate size proteins (as aggregates or degradation products) were seen in the samples from the transgenic plant.

EXAMPLE 2

Hybridoma Preparation

Mice were immunized with purified AAD-1, and standard fusion techniques were used to prepare a panel of hydridomas expressing anti AAD-1 monoclonal antibodies. Samples of spent tissue culture media were removed aseptically from each well containing a hybridoma culture and assayed for AAD-1 reactivity using the following antibody capture ELISA method. Microtiter wells were coated with a solution of 1-10 µg/mL of purified AAD-1. The wells were washed and samples of spent tissue media were placed in the wells and allowed to incubate. The wells were washed and horseradish peroxidase-labeled goat anti mouse antiserum was added and allowed to incubate. The plates were washed, substrate was added to develop a color reaction and the plates were read for OD (optical density). Wells with high OD readings were mapped back to culture wells containing the hybridomas. The AAD-1 antibody positive cultures were continually screened for antibody production to assure growth stability and antibody production as the cultures were expanded. Several rounds of limiting dilution cloning were performed to establish true monoclonality for each culture. Further assays on antibody positive clones were conducted to determine the suitability of each antibody for use in the presently claimed quantitative detection methods for field use with plant material.

EXAMPLE 3

Assay Development

Assay conditions were evaluated for the optimal coating concentration, coating buffer constituents, coating format and pH, and antibody-biotin ratio and concentrations. The final assay format used a sequential or simultaneous sandwich format. Both HRP (horse radish peroxidase) and AP (alkaline phosphatase) labeled systems were developed. mAb 473F274.2#36 was coated and dried on the surface of the reaction wells for both systems.

In the HRP system, the mAb 473F185.2#18 was conjugated to HRP. AAD-1 sample were added to reaction wells and incubated for 1 hour at room temperature. Following a wash step, the 473F185.2#18-HRP conjugate was added to the reaction wells and incubated for 30 minutes at room temperature. The reaction wells were then washed and substrate was added to react with the HRP. In the presence of AAD-1 protein, the HRP conjugate bound to the reaction wells and subsequently generated a color change with the substrate in the wells. After a 30 minute substrate incubation period, a stop solution was added and the reaction wells were read in a 96 well plate reader at a wavelength of 450 nm minus 650 nm.

Figure 1:
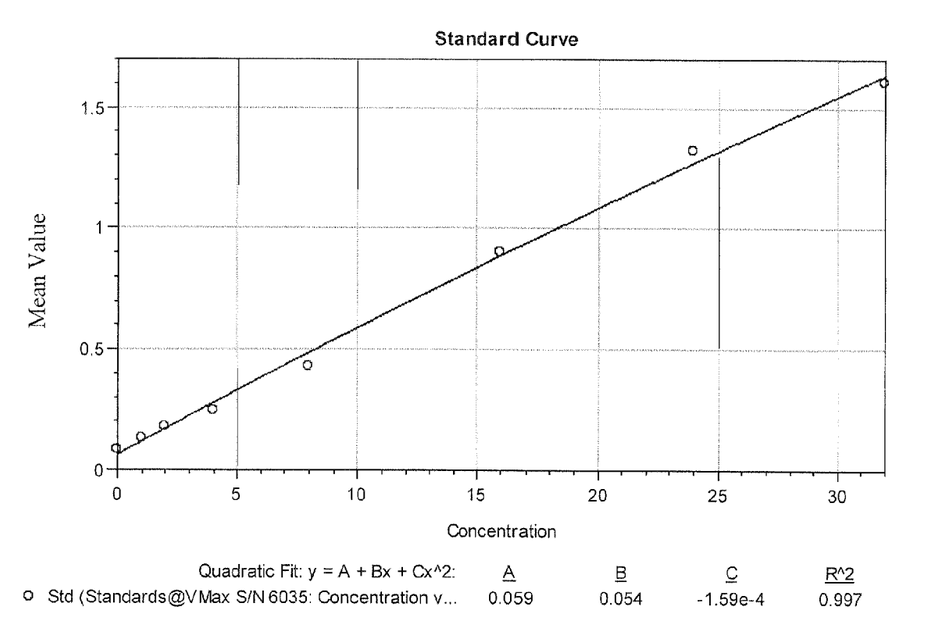
FIG. 1: AAD-1 Standard Curve (alkaline phosphatase (AP) detection): In the AP system, the 473F185.2#18 mAb was conjugated to biotin. A sample and the biotinylated mAb were added to the reaction wells and incubated for 1 hour at room temperature. Following a wash step, streptavidin-AP conjugate was added to the reaction wells and incubated for 30 minutes at room temperature. The reaction wells were then washed and substrate was added to react with the AP. In the presence of AAD-1 protein, the AP conjugate bound to the reaction wells and subsequently generated a color change with the substrate in the well. After a 30 minute substrate incubation period, the reaction was read in a 96 well plate reader at a wavelength of 405 nm, the results of which were plotted and a standard curve was calculated.

In the AP system, the 473F185.2418 mAb was conjugated to biotin. A sample and the biotinylated mAb were added to the reaction wells and incubated for 1 hour at room temperature. Following a wash step, streptavidin-AP conjugate was added to the reaction wells and incubated for 30 minutes at room temperature. The reaction wells were then washed and substrate was added to react with the AP. In the presence of AAD-1 protein, the AP conjugate bound to the reaction wells and subsequently generated a color change with the substrate in the well. After a 30 minute substrate incubation period, the reaction was read in a 96 well plate reader at a wavelength of 405 nm, the results of which were plotted and a standard curve was calculated as shown in FIG. 1.

During testing of the HRP-based assay, a non-specific signal was observed with maize tissue samples. In contrast, the AP system did not demonstrate any significant non-specific signal when using maize tissues. Therefore the AP-based assay is the more preferred format; though, the HPR-based assay is nonetheless a viable system.

EXAMPLE 4

Assay Characteristics

The resulting AP format was evaluated with different lots of reagents to determine the sensitivity and range of the assay as well as to establish the absorbance variability and accuracy of the assay. In these studies, three operators tested two plate/reagent lots by running two standard curves and single point analyses. The overall absorbance of the assay's standard curve ranged from 0.1 $abs_{405}$ to 1.5 $abs_{405}$. The results are shown in Table 1 below.

TABLE 1

| AAD-1 Conc. | Analyst 1 OD | % CV | Analyst 2 OD | % CV | Analyst 3 OD | % CV |
|---|---|---|---|---|---|---|
| Lot A Reagent | | | | | | |
| 0 | 0.055 | 1.7 | 0.050 | 2.7 | 0.046 | 4.4 |
| 1.56 | 0.119 | 1.0 | 0.112 | 0.5 | 0.1112 | 2.9 |
| 3.12 | 0.189 | 0.8 | 0.176 | 3.0 | 0.180 | 2.6 |
| 6.25 | 0.341 | 2.5 | 0.310 | 3.3 | 0.322 | 3.3 |
| 12.5 | 0.881 | 14.8 | 0.622 | 3.1 | 0.653 | 2.0 |
| 25 | 1.457 | 2.8 | 1.361 | 2.1 | 1.429 | 2.1 |
| Lot B Reagent | | | | | | |
| 0 | 0.053 | 3.6 | 0.054 | 3.2 | 0.048 | 2.9 |
| 1.56 | 0.125 | 1.7 | 0.117 | 2.1 | 0.112 | 2.7 |
| 3.12 | 0.197 | 1.0 | 0.188 | 4.6 | 0.177 | 2.7 |
| 6.25 | 0.353 | 2.0 | 0.355 | 1.6 | 0.319 | 3.3 |
| 12.5 | 0.709 | 2.1 | 0.833 | 4.2 | 0.639 | 3.4 |
| 25 | 1.520 | 1.5 | 1.518 | 8.9 | 1.429 | 3.1 |

The effective quantitative range of the assay ranged from 1 ng/mL to 32 ng/mL with an average inter-plate and inter-analyst % error and percent coefficient of variation (% CV) of 3.40% and 2.62%, respectively (Table 2). There was no significant effect of operator, plate lot, conjugate lot or day on the % CV determinations. Inter-plate lot % error and accuracy were very similar to the intra-plate lot results (Tables 3 and 4).

TABLE 2

| | Measured AAD-1 | | | |
|---|---|---|---|---|
| AAD-1 ng/mL | Predconc ng/mL | % error | % CV | n |
| 0 | 0.00 | — | — | 15 |
| 1 | 0.91 | 9.00 | 2.14 | 15 |
| 2 | 2.00 | 0.0 | 3.32 | 15 |
| 4 | 3.91 | 2.25 | 2.41 | 15 |
| 8 | 8.56 | 7.00 | 1.29 | 15 |
| 16 | 16.36 | 1.00 | 2.45 | 15 |
| 24 | 23.15 | 3.54 | 3.02 | 15 |
| 32 | 32.32 | 1.00 | 3.73 | 15 |
| Mean | — | 3.40 | 2.62 | 120 |

TABLE 3

| | Plate Lot 1 | Plate Lot 2 | Plate Lot 3 | Overall Lots |
|---|---|---|---|---|
| Mean OD | 0.629 | 0.760 | 0.671 | 0.669 |
| Stdev | 0.026 | 0.043 | 0.033 | 0.034 |
| % CV | 4.1 | 5.7 | 4.9 | 5.0 |
| range | 0.601-0.724 | 0.649-0.793 | 0.630-0.741 | 0.601-0.793 |
| n | 96 | 96 | 96 | 288 |

TABLE 4

| AAD-1 (ng/mL) | Mean OD | Stdev | % CV |
|---|---|---|---|
| 0 | 0.093 | 0.005 | 5.4 |
| 1 | 0.141 | 0.006 | 4.3 |
| 2 | 0.186 | 0.010 | 5.4 |
| 4 | 0.261 | 0.007 | 2.7 |
| 8 | 0.440 | 0.018 | 4.1 |
| 16 | 0.735 | 0.048 | 6.5 |
| 24 | 1.109 | 0.037 | 3.3 |
| 32 | 1.529 | 0.026 | 2.4 |

EXAMPLE 5

Assay Specificity

The immunoassay of Example 3 was run against deregulated commercial trait proteins to determine if there was any unacceptable cross reactivity. Test samples containing proteins Cry1Ab, Cry1Ac, Cry 1F, Cry34Ab1, Cry35Ab1, and PAT (phosphinothricin acetyltransferase) were incubated in the reaction wells and the immunoassay was run according to Example 3. Similarly, transgenic corn seed expressing Cry1F (DAS TC1507), Cry34Ab1/35Ab1 (DAS-59122-7), Cry3Bb (MON 863), Cry2Ab/Cry1A (MON 89034), Cry3Bb/CP4 (MON 88017), GA21 (GA21), Cry1Ab (MON 810 and Btl1), Cry3A (MIR604), and CP4 (NK603) were run in the immunoassay and did not generate a positive signal. The assay was found to be highly selective for AAD-1 protein. No cross reactivity or interfering effects were measured for the non-target proteins in tests. Therefore, it was concluded that the claimed assay AAD-1 Microtiter Plate ELISA had no cross-reactivity to other recombinant proteins found in commercially available transgenic varieties of corn.

EXAMPLE 6

AAD-1 Quantitative ELISA Protocol

1. General Requirements
   A. Materials
   Bead, 1/8" chrome steel, catalog number BS-0125-C, Small Parts Inc., Miami Lakes, Fla. or equivalent.
   Cap, for 2.0-mL conical tube, catalog number 02-681-361, Fisher Scientific or equivalent
   Multi-channel pipettor, 12-channel, 10-300
   Pipette tips, various sizes
   Plate covers or equivalent
   Reagent reservoirs, non-sterile
   Single channel pipettors of various sizes, 10 μL-1.0 mL
   Tubes, polypropylene, 5 mL, catalog number 14-956-1D, Fisher Scientific
   Tube, 15-mL polypropylene centrifuge with cap, catalog number 05-539-12, Fisher Scientific
   Tube, 2.0-mL conical micro-centrifuge, catalog number 02-681-344, Fisher Scientific
   U-bottom plates, nonbinding 96-well, BD Falcon catalog no. 35-3918 or equivalent
   B. Equipment
   Balance, analytical, Model AB54-S, Mettler Instrument Corporation or equivalent
   Centrifuge, capable of holding 2-mL Eppendorf tubes, Eppendorf-5417C or equivalent
   Freezer, capable of maintaining −20° C., Model 75F, U-Line Corporation, Milwaukee, Wis. or equivalent
   Plate reader, capable of reading 405-650 nm, Molecular Devices catalog no. 0200-2018 or equivalent
   Refrigerator, capable of maintaining temperature at 2-8° C.
   Vortex, Genie-2 Model, catalog number 12-812, Fisher Scientific or equivalent Shaker/Grinder, Model Geno/Grinder, catalog number 2000-115, Certiprep, Metuchen, N.J. or equivalent Washer, 96-well microplate, Model Elx 405, Bio-Tek Instruments, Inc. or equivalent 2. Reagents and Reagent Preparation
   A. Antibody coated 96-well microtiter plates; AAD-1 Antibody Conjugate (120 mL); color Reagent (120 mL); Stop Solution (120 mL).
   B. PBST, pH 7.4, catalog number P-3563, Sigma. Store at 2-8° C.
   C. Phosphate-Buffered Saline+0.05% TWEEN-20 (PBST), pH 7.4. Store at 2-8° C. for up to 6 months. PBST powder may be used to prepare the buffer, catalog number P-3563, Sigma.
   D. 30% Bovine Serum Albumin (BSA) solution, Immunohematology grade (Serologicals Corporation, Inc. 1-800-431-4505 Catalog No. 81-070 or equivalent. Store at 2-8° C.
   E. AAD-1 standard protein.
   F. Assay Buffer: PEST plus 0.5% BSA (w/v) (PBST/BSA). PBST powder may be used to prepare the buffer, catalog number P-3563, Sigma.
      Add 1 mL of 30% BSA to the 30 mL PBST in the container;
      Mix well and it can be used for the day. Discard the remaining after the experiment.
   G. Washing Buffer: PBST plus 0.05% TWEEN®-20 (w/v). PBST powder may be used to prepare the buffer, catalog number P-3563, Sigma.
      Add 0.5 mL of TWEEN®-20 to the 1 L PBST in the container;
      Mix well and store at room temperature. Discard the solution if any visible contamination is observed.
   H. AAD-1 Stock Solution, 1000 ng/mL.
      Prepare a 1000-ng/mL stock solution based on the liquid standard concentration in PBST/BSA. Keep it in ice to be used within 2 hours. Discard if any visible contamination is observed. Discard the remainder AAD-1 stock; do not re-freeze it for reuse.

3. Procedure
   A. Bring ELISA reagents to 20-25° C. by removing them from the refrigerator at least 30 minutes prior to performing the assay.
   B. Prepare the AAD-1 standards in Assay Buffer in 5-mL polystyrene tubes as follows. Vortex a few seconds before transferring to next dilution. Store the tubes on ice; prepare new standards for each assay immediately before adding samples to the plate. (Note: when transferring stock reference antigen, please rinse the pipet tip once in the destination solution after dispense).

| Conc. of Stock Soln. ng/mL | Aliquot of Stock Soln. µL | Starting Buffer Volume µL | Final Soln. Volume µL | Final Standard Conc. ng/mL | Remaining Volume after Aliquot[a] µL |
| --- | --- | --- | --- | --- | --- |
| 1000 | 25 | 1225 | 1250 | 20.00 | 450 |
| 20.00 | 800 | 800 | 1600 | 10.00 | 400 |
| 10.00 | 1200 | 300 | 1500 | 8.00 | 600 |
| 8.00 | 900 | 300 | 1200 | 6.00 | 500 |
| 6.00 | 700 | 350 | 1050 | 4.00 | 550 |
| 4.00 | 500 | 500 | 1000 | 2.00 | 500 |
| 2.00 | 500 | 500 | 1000 | 1.00 | 500 |
| 0 | 0 | 500 | 500 | 0 | 500 |

[a]The final solution volume is the remaining volume in the container after it has served as the stock solution for the next standard concentration and the relevant amount of solution is transferred.

C. Prepare test samples:
      For fresh leaf samples, make 4 leaf punches and place into 2-mL polypropylene tubes. Add two or three metal beads to each tube. Then add 0.80 mL of the Assay Buffer. Cap all the tubes.
      Extract the samples using the Geno/Grinder automatic shaker/grinder at a dial setting of 350 and the toggle switch at the 1× setting (approximately 1500 strokes per minute) for 5 minutes as one cycle. An alternative equivalent grinding or extraction method may be used.
      Centrifuge the samples at 14,000 (or greater) rpm for 5 minutes or until separated (no visible particles in the supernatant). The supernatant can be transferred to a separate tube or aliquoted for analysis. Keep the solution on ice and assay it within 2 hours.
   D. Add the AAD-1 samples to ELISA plate(s) as follows:
      Transfer the ELISA standard dilutions to Columns 1-3 on a non-binding 96-well U-bottom microtiter plate (approximately 130 µl/well). For each plate tested, run standard solutions in triplicate.
      Prepare sample dilutions as needed and transfer diluted samples to the non-binding 96-well microtiter plate (130 µL/well) containing the standard calibration solutions and record the location on the 96-well assay template sheet.
   E. Cover the pre-coated plate, and gently swirl on the benchtop or a plate shaker for approximately five seconds to mix. Allow to incubate at ambient temperature for 1 hour (±5 min).
   F. Wash the pre-coated plate 3-5 times by filling each well with PBST. Tap out excess liquid on a paper towel. It may be washed by plate washer.
   G. Pipet 100 µL of the AAD-1 antibody conjugate to each well of the antibody coated 96-well microtiter plate. Then transfer 100 µL of the ELISA standard solutions and diluted samples from the U-bottom microtiter plate to a pre-coated plate, keeping the same orientation as the samples are transferred to the pre-coated plate. Change pipette tips with each row.
   H. Cover the plate and place it on a shaker and incubate at ambient temperature for 30 min (±5 min).
   I. Wash the plate 3-5 times by filling each well with washing buffer. Tap out excess liquid on a paper towel. It may be washed by plate washer.
   J. Add 100 µL of the TMB substrate to each well of the reaction plate. Cover and gently mix. Allow to incubate at ambient temperature in the dark for 20±2 minutes.
   K. Add 100 µL of Stop Solution to each well to stop the reaction. Mix the plate gently and read the absorbance at duel wavelength module 450 nm-650 nm using the MAXline Vmax plate reader.
   L. Save the raw data file and do the data analysis as described in Section 4.

4. Data Analysis and Calculation
   A. Calibration Curve:
      Absorbance values from the reference standards should be used to develop a calibration curve. SOFTmax PRO™ software or Microsoft Excel is used to provide necessary analysis and calculation. The calibration curve for the AAD-1 ELISA is constructed using a quadratic regression of the expected concentrations of the standards and their subsequent absorbance (optical density).

B. The equation fits the best parabola to the standard curve based on the equation:

$y=A+Bx+Cx^2$

Where:
  y=mean absorbance value (OD)
  x=reference standard concentration
C. Calculation of AAD-1 in Test Samples:
  SOFTmax PRO™ or Microsoft Excel can be used to calculate the AAD-1 concentration of each test sample. The predicted concentration is determined using the coefficients of the curve and optical density (OD) readings in the quadratic equation. The regression equation is applied as follows:

$$\text{Predicted concentration} = \frac{-B + \sqrt{B^2 - 4C*(A-OD)}}{2C}$$

The determined AAD-1 concentration of a test sample (i.e., the individual replicates of a single dilution) is obtained by multiplying the predicted concentration by the dilution factor used.

5. Criteria for Acceptance of an Analytical Batch
  Each analytical batch shall meet the accept criteria in the procedure to be valid as listed below. If the data fail to meet these performance criteria, the analyst should evaluate the results, determine the potential source of the variation, and repeat the analysis if necessary.

| | |
|---|---|
| Assay Buffer Blank | Absorbance 450 nm-650 nm <0.150 |
| 0-ng/mL standard | Absorbance 450 nm-650 nm <0.150 |
| 20-ng/mL standard | Absorbance 450 nm-650 nm ≥0.85 |
| Calibration curve | $r^2$ (Correlation of determination) >0.990 |
| All positive reference standards, OD | CV (OD) of triplicates ≤15% |
| Unknown or QC samples, solution | CV (OD) of replicates ≤20% |
| Quality control samples, solution (if applicable) | Measured value ≤±20% expected value |

What is claimed is:

1. An isolated monoclonal antibody that specifically binds to an aryloxyalkanoate-1 dioxygenase enzyme (AAD-1), wherein the monoclonal antibody is produced by a hybridoma on deposit with the American Type Culture Collection (ATCC) under an Accession Number selected from the group consisting of PTA-11251 (473F185.2#18), PTA-11252 (473F225.2#7), PTA-11253 (73F274.21136) (473F274.2#36), PTA-11254 (473H46.2), and PTA-11255 (473H172.3).

2. The monoclonal antibody of claim 1 produced by the hybridoma having Accession Number PTA-11251 (473F185.2#18).

3. The monoclonal antibody of claim 1 produced by the hybridoma having Accession Number PTA-11252 (473F225.2#7).

4. The monoclonal antibody of claim 1 produced by the hybridoma having Accession Number PTA-11253 (473F274.2#36).

5. The monoclonal antibody of claim 1 produced by the hybridoma having Accession Number PTA-11254 (473H46.2).

6. The monoclonal antibody of claim 1 produced by the hybridoma having Accession Number PTA-11255 (47311172.3).

7. A hybridoma cell line that produces a monoclonal antibody of claim 1 and is on deposit with the American Type Culture Collection (ATCC) under an Accession Number selected from the group consisting of PTA-11251 (473F185.2#18), PTA-11252 (473F225.2#7), PTA-11253 (473F274.2#36), PTA-11254 (4731146.2), and PTA-11255 (473H172.3).

8. The hybridoma cell line of claim 7 deposited under ATCC Accession Number PTA-11251 (473F185.2#18).

9. The hybridoma cell line of claim 7 deposited under ATCC Accession Number PTA-11252 (473F225.2#7).

10. The hybridoma cell line of claim 7 deposited under ATCC Accession Number PTA-11253 (473F274.2#36).

11. The hybridoma cell line of claim 7 deposited under ATCC Accession Number PTA-11254 (473H46.2).

12. The hybridoma cell line of claim 7 deposited under ATCC Accession Number PTA-11255 (473H172.3).

13. A method for identifying the presence of AAD-1 enzyme, comprising:
  a) immobilizing a first monoclonal antibody of claim 1 onto an assay surface, and then washing said assay surface;
  b) contacting said assay surface with a liquid suspected of containing AAD-1 enzyme for a period of time sufficient to allow binding, and then washing said assay surface;
  c) contacting said assay surface with a different second antibody of claim 1 conjugated to a reporting group for a period of time sufficient to allow binding of said second conjugated monoclonal antibody, and then washing said assay surface; and,
  d) detecting the presence or absence of said reporting group, wherein the presence of said reporting group indicates the presence of AAD-1 enzyme in the liquid.

14. A method for the quantitative determination of AAD-1 enzyme, comprising:
  a) immobilizing an AAD-1 antiserum onto an assay surface;
  b) contacting said assay surface with a liquid suspected of containing AAD-1 enzyme for a period of time sufficient to allow binding, and then washing said assay surface;
  c) contacting said assay surface with a monoclonal antibody of claim 1 conjugated to a reporting group for a period of time sufficient to allow binding of said conjugated monoclonal antibody, and then washing said assay surface; and
  d) quantifying the presence of said reporting group by comparison to a calibration curve, wherein the presence of said reporting group indicates the presence of AAD-1 enzyme in the liquid.

15. The method of claim 14 wherein the conjugated monoclonal antibody is produced by the hybridoma cell line having ATCC Accession Number PTA-11251 (473F1852#18).

16. A monoclonal antibody that specifically binds to an aryloxyalkanoate-1 dioxygenase enzyme (AAD-1) labeled with a reporting group, wherein the monoclonal antibody is produced by a hybridoma on deposit with the American Type Culture Collection (ATCC) under an Accession Number selected from the group consisting of PTA-11251 (473F185.2418), PTA-11252 (473F225.2#7), PTA-11253 (473F274.2#36), PTA-11254 (473H46.2), and PTA-11255 (473H172.3).

17. The monoclonal antibody of claim 16, wherein said reporting group is a radioisotope or an enzyme.

18. An isolated monoclonal antibody that specifically binds to an aryloxyalkanoate-1 dioxygenase enzyme (AAD-1) immobilized on a surface, wherein the monoclonal antibody is produced by a hybridoma on deposit with the American Type Culture Collection (ATCC) under an Accession Number selected from the group consisting of PTA-11251 (473F185.2#18), PTA-11252 (473F225.2#7), PTA-11253 (473F274.2#36), PTA-11254 (473H46.2), and PTA-11255 (47311172.3).

19. The isolated antibody of claim 18, wherein said monoclonal antibody is covalently coupled to said surface.

* * * * *

UNITED STATES PATENT AND TRADEMARK OFFICE
CERTIFICATE OF CORRECTION

PATENT NO. : 8,673,583 B2  
APPLICATION NO. : 13/218498  
DATED : March 18, 2014  
INVENTOR(S) : Shawna K. Embrey et al.

Page 1 of 2

It is certified that error appears in the above-identified patent and that said Letters Patent is hereby corrected as shown below:

In the Specification:

Column 1,  
Line 17, "2,4-dichiorophenoxyacetic" should read --2,4-dichlorophenoxyacetic--.  
Line 51, "dichlorophenixyacetic" should read --dichlorophenoxyacetic--.  
Line 63, "which naturally" should read --which are naturally--.

Column 5,  
Line 57, "Pisteataway," should read --Pistcataway,--.

Column 8,  
Line 43, "473F185.2418" should read --473F185.2#18--.

Column 10,  
Line 44, "10-300" should read --10-300 μL--.

Column 11,  
Line 11, "TWEEN-20" should read --TWEEN®-20--.  
Line 20, "PEST plus" should read --PBST plus--.

In the Claims:

Column 13,  
Lines 50-51, "PTA-11253 (73F274.21136) (473F274.2#36), PTA-11254" should read  
         --PTA-11253 (473F274.2#36), PTA-11254--.  
Line 67, "(47311172.3)." should read --(473H172.3).--.

Signed and Sealed this  
Twenty-first Day of October, 2014

Michelle K. Lee  
*Deputy Director of the United States Patent and Trademark Office*

CERTIFICATE OF CORRECTION (continued)
U.S. Pat. No. 8,673,583 B2

Column 14,
Line 6, "(4731146.2)," should read --(473H46.2),--.
Line 59, "(473F185.2418)," should read --(473F185.2#18),--.

Column 15,
Line 5, "(47311172.3)." should read --(473H172.3).--.